United States Patent [19]

Kanai et al.

[11] 4,069,253

[45] Jan. 17, 1978

[54] PROCESS FOR THE PRODUCTION OF WATER-FREE MOLTEN UREA

[75] Inventors: Kazumichi Kanai, Fujisawa; Tetsuo Kimura, Kamakura; Akito Fukui, Chiba, all of Japan

[73] Assignees: Mitsui Toatsu Chemicals, Incorporated; Toyo Engineering Corporation of Japan, both of Tokyo, Japan

[21] Appl. No.: 656,010

[22] Filed: Feb. 6, 1976

Related U.S. Application Data

[63] Continuation of Ser. No. 155,230, June 21, 1971, abandoned.

[30] Foreign Application Priority Data

July 1, 1970  Japan ................................ 45-57413

[51] Int. Cl.² ........................................... C07C 126/00
[52] U.S. Cl. .............................. 260/555 C; 260/555 R; 203/12

[58] Field of Search ...................... 260/555 C; 203/12; 23/274, 775, 776

[56] References Cited

U.S. PATENT DOCUMENTS

| | | | |
|---|---|---|---|
| 1,584,875 | 5/1926 | Lidholm | 260/555 C |
| 2,961,464 | 11/1960 | Kaasenbrood | 260/555 C |
| 3,124,612 | 3/1964 | Cook | 260/555 C |
| 3,147,174 | 9/1964 | Cook | 260/555 C |
| 3,171,770 | 3/1965 | Biekart et al. | 260/555 C |
| 3,223,145 | 12/1965 | Templeton et al. | 260/555 C |
| 3,585,237 | 6/1971 | Terrana et al. | 260/555 C |

*Primary Examiner*—O. R. Vertiz
*Assistant Examiner*—Eugene T. Wheelock
*Attorney, Agent, or Firm*—Fisher, Christen & Sabol

[57] ABSTRACT

An aqueous urea solution is concentrated to a substantially water-free molten urea by conducting successively a first step of concentrating said aqueous urea solution under the conditions forming a urea slurry and a second step of concentrating said urea slurry under conditions forming a substantially water-free molten urea free from crystalline urea.

6 Claims, No Drawings

PROCESS FOR THE PRODUCTION OF WATER-FREE MOLTEN UREA

This is a continuation, of application Ser. No. 155,230, filed June 21, 1971 now abandoned.

This invention relates to a process for concentrating an aqueous urea solution, and more particularly it relates to an improved process for evaporating an aqueous urea solution obtained by separating unreacted ammonium carbamate from the urea synthesis melt to a substantially water-free molten urea.

In the manufacture of molten urea applicable to prilling, there has been hitherto used a process in which the unreacted ammonium carbamate is separated from the urea synthesis melt obtained by reacting carbon dioxide and ammonia at a urea synthesis temperature and pressure, the resulting aqueous urea solution of 50 - 80% is concentrated and subjected to crystallization to yield urea crystals and the urea crystals are melted in a melter, or a process in which the aqueous urea solution as mentioned above is concentrated up to a substantially water-free molten urea by means of, for example, an evaporater of the falling film type.

In the former process, it is possible to concentrate at a relatively low temperature and, therefore, use the heat of the low temperature level generated in the urea manufacturing system as the heat source for the concentration, since the vacuum evaporation can be used and the crystallization of urea can be allowed. Therefore, advantageously, the amount of steam used may be saved and the amount of biuret in the product is lowered. Disadvantageously, the apparatus required for separating the crystalline urea from the mother liquid comprises a dryer for the crystalline urea, a melter for melting the dried urea, and other equipment resulting in a large equipment investment.

On the other hand, in the latter process, though it is better in the equipment investment than the former process, the temperature of aqueous urea solution concentrated should be kept more than the temperature at which a saturated urea solution is formed as shown in the table 1, since the aqueous urea solution is concentrated without the crystallization of urea.

carbamate to yield a substantially water-free molten urea, a steam pressure of 5 - 10 kg/cm² (gauge) is required industrially as the heat source. Even on concentrating up to 88% in the first stage and then up to a substantially water-free molten liquid urea in the second stage, it is required a steam pressure of 2 - 5 kg/cm² (gauge) for the first concentration and a steam pressure of 5 - 10 kg/cm² (gauge) for the second concentration, so that 0.4 - 0.5 tons of expensive high pressure steam may be required for the manufacture of one ton of urea. Moreover, the content of biuret in the product is disadvantageously high due to the concentration at a higher temperature.

An object of this invention is to provide a process for concentrating an aqueous urea solution to a substantially water-free molten urea with less consumption of high pressure steam and lower equipment investment.

Another object of this invention is to provide a process for concentrating an aqueous urea solution to a substantially water-free molten urea with less biuret production and less hydrolysis of urea.

According to this invention, there is provided a process for concentrating an aqueous urea solution up to a substantially water-free molten urea which comprises the combination of a first step of concentrating said aqueous urea solution under the conditions forming an aqueous urea solution containing crystalline urea (urea slurry) and a second step of concentrating said aqueous urea solution containing crystalline urea under the conditions forming a substantially water-free molten urea free from crystalline urea.

The first concentration step according to this invention is based on the fact which shall be mentioned hereunder. That is, it is seen that the content of urea in an aqueous urea solution containing urea crystals at a temperature is always higher than that of an aqueous urea solution free from urea crystals at the same temperature — in other words, a concentration of urea can be obtained at a lower temperature in an aqueous urea solution containing crystalline urea than in an aqueous solution of urea free from it. The fact is obviously understood by the comparison of table 1 with the table 2, in which the content of urea (% by weight) in the slurry containing 40% by weight of crystalline urea preferred Table 1 *)

| Temperature ° C | Urea concentration in saturated solution [% by weight] | Saturated vapor pressure of water on saturated urea solution [mmHg] |
|---|---|---|
| 40 | 62.5 | 38 |
| 60 | 71.0 | 82 |
| 80 | 80.2 | 152 |
| 100 | 88.0 | 250 |
| 120 | 96.0 | 304 |
| 132.7 | 100.0 | — |

*) According to M. Frejacques: Chimie & Industrie, 60 28 (1948)

As obviously seen from the table 1, since it should be heated at least more than 132.7° C in order to concentrate in one stage the aqueous urea solution obtained through the decomposition of unreacted ammonium to the total weight and the saturated vapor pressure of water on an aqueous saturated solution of urea (mmHg) are plotted at every temperature.

Table 2

| Temperature ° C | Content of urea* [% by weight] | Saturated vapor pressure of water on saturated urea solution [mmHg] |
|---|---|---|
| 40 | 77.5 | 38 |
| 60 | 82.6 | 82 |
| 80 | 88.1 | 152 |
| 100 | 92.8 | 250 |
| 120 | 97.6 | 304 |
| 132.7 | 100.0 | — |

*Calculated from the following equation based on the data of Table 1:

Table 2-continued

| Temperature ° C | Content of urea* [% by weight] | Saturated vapor pressure of water on saturated urea solution [mmHg] |
| --- | --- | --- |

Content of urea (% by weight) =
$$\frac{\text{Weight of crystalline urea} + \text{Weight of urea dissolved}}{\text{Weight of crystalline urea} + \text{Weight of aqueous saturated solution of urea}} \times 100$$

For example, while it is necessary to heat more than 100° C to obtain an 88% by weight aqueous solution of urea free from crystalline urea, it can be attained at 80° C if the pressure of 40% by weight of crystalline urea is permitted. Accordingly, when the process of the concentration in the presence of crystalline urea according to this invention is used, the concentration up to a desired concentration can be attained at a lower temperature compared with the concentration in the absence of crystalline urea. Further, since there is contained crystalline urea in the first concentration step and the dissolution of crystalline urea takes place with the heat absorption in heating the urea slurry, the temperature elevation of the urea slurry is less than that of aqueous urea solution. This is very economical because a heat exchanger which utilizes a heat source at a relatively low temperature can be used. For example, while the temperature of 100 kg/hr of aqueous saturated solution of urea at 80° C is elevated to 121.7° C when given a heat of 3200 Kcal/hr, the temperature elevation of aqueous urea solution containing 30% by weight of crystalline urea is only 100.1° C. Compared with one-stage concentration processes, therefore, the heat source of a relatively low temperature level can be used for the concentration. For example, there may be used the heat of absorption generated in the absorption of unreacted ammonium carbamate separated as the mixture of ammonia and carbon dioxide by means of an absorbent; an excess reaction heat in the urea synthesis autoclave. To use these heat sources, steam may be generated by these heat sources and used as the heat source, or the absorption or the reaction may be conducted in indirect heat exchange relationship with (a) the aqueous urea solution to be concentrated — (b) a lower pressure steam of 0 – 2 kg/cm² (gauge) or (c) the waste heat from condensate of high pressure steam used for the separation of unreacted ammonium carbamate.

As to the operation conditions in the first concentration step, the lower limit of concentration temperature should be above 40° C, preferably above 50° C because a larger concentrator is required if the saturated vapor pressure of water on the aqueous solution of urea is not more than a certain extent; the upper limit of concentration temperature should be less than the melting point of urea, i.e. 132.7° C, preferably below 120° C because there is no profit at a too high temperature compared with the conventional concentration under conditions maintaining the state of aqueous solution free from crystals. It is necessary from the view-point of fluidity of the concentrated aqueous urea solution that the permitted amount of crystalline urea in the effluent from the first evaporator is less than 70% by weight, preferably 10 – 60% by the weight of the the weight of urea slurry (the sum of weight of aqueous urea solution and the weight of the crystalline urea). The total content of urea in the urea slurry from the first concentration step is preferably 70 – 98% by weight, especially 75 – 95% by weight of the urea slurry. The concentration may be carried out under atmospheric pressure while passing an inert gas such as air or under a reduced pressure of 30 – 300 mmHg (absolute).

The aqueous saturated urea solution containing crystalline urea obtained in the first concentration step is brought to the second concentration step and concentrated in the state of aqueous urea solution free from crystals. That is, it is concentrated up to a substantially water-freee molten urea at a temperature above the temperature at which an aqueous saturated urea solution is formed in the second concentration step. The step is, so to speak, the finishing step of concentration and the solution at the inlet of this step may contain crystalline urea. The temperature at the outlet of this step is more than the melting point of urea, preferably a temperature between the melting point of urea and 150° C. The pressure is atmospheric or less and the concentration may be carried out while passing an inert gas such as air. A known evaporator of the falling film type is used preferably for the concentration. The molten urea from the second concentration step may contain less than about 1% by weight water.

The aqueous urea solution to be used in this invention may be obtained in any desired method. For example, it may be the aqueous urea solution which is obtained by removing the unreacted ammonium carbamate from the urea synthesis melt containing urea, water and unreacted ammonium carbamate, said urea synthesis melt being obtained by reacting ammonia with carbon dioxide at the urea forming temperature and pressure. In order to remove the unreacted ammonium carbamate from the urea synthesis melt, for example, the synthesis melt may be subjected to a distillation at approximately atmospheric pressure or to distillations in which pressures are decreased successively in two or three stages thereby decomposing the unreacted ammonium carbamate into ammonia and carbon dioxide in each stage for separation from the aqueous urea solution. Alternatively, the urea synthesis melt may be stripped, at a pressure the same as or lower than the urea synthesis pressure, with carbon dioxide, ammonia or an inert gas. The aqueous urea solution may be also obtained by separating urea as the urea adduct from the urea synthesis and decomposing the adduct into an aqueous urea solution and an adduct forming agent.

According to this invention, a separator for separating crystalline urea from the mother liquid, a dryer for drying crystalline urea and a melter for melting crystalline urea are not needed resulting in a savings on equipment investment. Compared with the concentration in the state of aqueous urea solution free from urea crystals, the first concentration step can be carried out at a lower temperature than that of the former in order to obtain a urea slurry of the same urea content, so that a heat source at a relatively low temperature such as a low pressure steam, a condensate of high pressure steam and a heat in the urea production system can be used. Therefore, the amount of expensive high pressure steam can be saved. Further, as aforementioned, the heat exchanger for the heating in the first concentration step is designed very readily since the step is carried out in the presence of crystals. Moreover, the hydrolysis of urea and the amount of biuret formed are reduced compared with the concentration in the state of aqueous urea solution.

The following are examples further illustrating the present invention, but this invention is not to be restricted to the following concrete examples only. In the examples, percentages are by weight.

EXAMPLE I

An aqueous urea solution consisting of 71.6% of urea, 0.2% of ammonia, 0.1% of carbon dioxide, 27.8% of water and 0.3% of biuret, which was obtained by subjecting the urea synthesis melt from the urea synthesis autoclave to a high and low pressure distillation to remove the unreacted ammonium carbamate, was introduced into the first concentration vessel to concentrate at 80° C and 152 mmHg (absolute). The urea slurry containing 39.1% of crystalline urea of the total weight from the first concentrator (said slurry consisting of 87.7% urea, 0.1% of ammonia, 0.1% of carbon dioxide, 11.7% of water and 0.4% of biuret) was heated to 100° C through a heater to dissolve completely the crystalline urea and introduced into the second concentrator of falling film type and the substantially whole water contained was evaporated while passing air. The molten urea at 135° C from the second concentrator was dropped as droplets through the nozzles at the top of a prilling tower to yield prilled urea.

For the concentration, 23 kg of steam of 1 kg/cm$^2$ (gauge) obtained from the waste heat recovery were used per 100 kg of product for the first concentrator and the heater for dissolving the crystalline urea in the urea slurry and 16 kg of steam of 5 kg/cm$^2$ (gauge) for the second concentrator. The amount of urea hydrolyzed and the amount of biuret formed per 100 kg of product were 0.3 kg and 0.3 kg respectively in the second concentrator and negligible in the first concentrator.

For comparison, the aqueous urea solution as mentioned above was concentrated by means of a falling film type concentrator in one stage while passing air. The resulting substantially water-free molten urea at 135° C was prilled in the same manner as mentioned above to yield prilled urea. For the concentration, 40 kg of steam of 5 kg/cm$^2$ (gauge) were used per 100 kg of product. The amount of urea hydrolyzed and the amount of biuret formed in the concentrator were 1 kg and 0.6 kg respectively.

The aqueous urea solution as mentioned above was also concentrated at an outlet temperature of 105° C in the first concentration step by means of falling film type evaporator while passing air to yield an aqueous urea solution consisting of 87.7% of urea, 0.1% of ammonia, 0.1% of carbon dioxide, 11.4% of water and 0.7% of biuret. The resulting aqueous urea solution was concentrated at an outlet temperature of 135° C in the second concentration step by means of a falling film type evaporator to yield a substantially water-free molten urea and the molten urea was prilled in the same manner as mentioned above to yield prilled urea. For the concentration, 24 kg of steam of 3 kg/cm$^2$ (gauge) was required per 100 kg of product in the first concentrator and 15.5 kg of steam 5 kg/cm$^2$ (gauge) in the second concentrator. The amount of urea hydrolyzed and the amount of biuret formed per 100 kg of product were 0.6 kg and 0.3 kg in the first concentrator and 0.3 kg and 0.3 kg in the second concentrator respectively.

As mentioned above, compared with the previous methods, 24 kg of steam 3 kg/cm$^2$ (gauge) or 5 kg/cm$^2$ (gauge) were saved per 100 kg of product, the loss of urea due to the hydrolysis is reduced and a product of small biuret content is obtained by using the process according to this invention.

EXAMPLE II

An aqueous urea solution having the same composition as in Example I was introduced into the first concentrator maintained at 75° C and 130 mmHg (absolute) and concentrated. The heat of absorption generated in the absorption of gaseous mixture of ammonia and carbon dioxide from the high pressure distillation by an absorbent was used as the heat source for the concentration. The resulting urea slurry (consisting of 86.0% of urea, 0.1% of ammonia, 0.1% of carbon dioxide, 13.4% of water and 0.4% of biuret) containing 38.5% of crystalline urea of total weight from the first concentrator was heated to 98° C through a heater to dissolve completely the crystalline urea, introduced into the second concentrator of the falling film type and then prilled in the same manner as in Example I to yield prilled urea.

23 kg of steam of 5 kg/cm$^2$ (gauge) were used per 100 kg of product for the heater for dissolving the crystalline urea in the slurry and for the second concentrator. The amount of urea hydrolyzed and the amount of biuret formed per 100 kg of product were 0.3 kg and 0.3 kg respectively in the second concentrator and negligible in the first concentrator.

What is claimed is:

1. A process for concentrating an aqueous urea solution to a substantially water-free molten urea which comprises subjecting said aqueous urea solution to a first evaporation in a first evaporation zone at a temperature of from 40° C to 120° C to form a urea slurry, said slurry comprising urea crystals suspended in a saturated solution of urea, said crystals being from 10 to 60 percent by weight of the weight of said urea slurry, and subjecting said urea slurry to a second evaporation in a second evaporation zone at a temperature above 132.7° C to dissolve the urea crystals and form a substantially water-free molten urea.

2. A process as claimed in claim 1 wherein said first evaporation is conducted at a temperature of from 50° to 120° C. and said second evaporation is conducted at a temperature of from 132.7° to 150° C.

3. A process as claimed in claim 1 wherein said first evaporation is conducted under a reduced pressure of from 30 to 300 mm Hg (absolute).

4. A process as claimed in claim 1 wherein said second evaporation is conducted while passing an inert gas through said urea slurry.

5. A process as claimed in claim 1 wherein said molten urea from said second evaporation contains less than about 1 percent by weight of water.

6. A process as claimed in claim 1 wherein the total content of urea in the urea slurry from said first evaporation is 70 to 98%.

* * * * *